(12) United States Patent
Okutani et al.

(10) Patent No.: US 12,274,578 B2
(45) Date of Patent: Apr. 15, 2025

(54) X-RAY IMAGING APPARATUS

(71) Applicant: Shimadzu Corporation, Kyoto (JP)

(72) Inventors: Keita Okutani, Kyoto (JP); Hiroshi Okumura, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 208 days.

(21) Appl. No.: 18/088,344

(22) Filed: Dec. 23, 2022

(65) Prior Publication Data
US 2023/0225692 A1 Jul. 20, 2023

(30) Foreign Application Priority Data

Jan. 18, 2022 (JP) .................................. 2022-005775

(51) Int. Cl.
*A61B 6/00* (2024.01)
*A61B 6/12* (2006.01)
*A61B 6/42* (2024.01)
*A61B 6/46* (2024.01)

(52) U.S. Cl.
CPC ............... *A61B 6/541* (2013.01); *A61B 6/12* (2013.01); *A61B 6/42* (2013.01); *A61B 6/463* (2013.01)

(58) Field of Classification Search
CPC .. A61B 6/541; A61B 6/12; A61B 6/42; A61B 6/463; A61B 6/46; A61B 6/4464; A61B 6/06; A61B 6/08; A61B 6/544; A61B 6/04; A61B 6/54; A61B 6/58
See application file for complete search history.

(56) References Cited

U.S. PATENT DOCUMENTS

| | | |
|---|---|---|
| 2015/0228071 A1 | 8/2015 | Jockel et al. |
| 2019/0183439 A1 | 6/2019 | Joerger et al. |
| 2020/0383655 A1 | 12/2020 | Fujii et al. |
| 2023/0016072 A1 | 1/2023 | Sugahara |
| 2023/0148986 A1 | 5/2023 | Feng et al. |

FOREIGN PATENT DOCUMENTS

| | | |
|---|---|---|
| CN | 111870268 A | 11/2020 |
| EP | 3135201 A1 | 3/2017 |
| EP | 3892200 A | 10/2021 |
| JP | 2020130753 A * | 8/2020 |
| JP | 2020-195733 A | 12/2020 |
| WO | 2021200000 A1 | 10/2021 |

OTHER PUBLICATIONS

Partial European Search Report dated May 26, 2023 in the correspondingEuropean patent application No. 23150914.2.
Extended European Search Report (EESR) dated Aug. 28, 2023 in the corresponding European patent application No. 23150914.2.
Extended European Search Report (EESR) dated Nov. 15, 2024 in the European Patent Application No. 24189418.7.

* cited by examiner

*Primary Examiner* — Kiho Kim
(74) *Attorney, Agent, or Firm* — Muir Patent Law, PLLC

(57) ABSTRACT

An X-ray imaging apparatus is provided with an X-ray irradiation unit, a detector, an image generation unit, an optical imaging unit for capturing an optical image, a storage unit for storing a trained model, the trained model being configured to output determination information to an input image based on the optical image, the determination information determining a state regarding an imaging range of a predetermined site of the subject or a relative position of the predetermined site to the other site of the subject, a control unit for acquiring the determination information, using the trained model, and a notification unit.

11 Claims, 6 Drawing Sheets

Determination information acquisition processing (Ex. 1)

Ex. 1

Generation of extraction image

Determination information acquisition processing (Ex. 2)

Ex. 2

Generation of estimation image

Determination information acquisition processing (Ex. 3)

Ex. 3

Modification 1

Modification 2

Generation of estimation image

X-RAY IMAGING APPARATUS

CROSS-REFERENCE TO RELATED APPLICATIONS

The related application number JP2022-005775, entitled "X-ray imaging apparatus" filed on Jan. 18, 2022, Keita Okutani, Hiroshi Okumura, upon which this patent application is based is hereby incorporated by reference in its entirety.

BACKGROUND OF THE INVENTION

Field of the Invention

The present invention relates to an X-ray imaging apparatus.

Description of the Related Art

Conventionally, an X-ray imaging apparatus for performing X-ray imaging on a subject is known. Such an apparatus is disclosed in, for example, Japanese Unexamined Patent Application Publication No. 2020-195733.

Japanese Unexamined Patent Application Publication No. 2020-195733 discloses an X-ray imaging apparatus provided with an X-ray irradiation unit for emitting X-rays, an X-ray detector for detecting X-rays, and an image processing unit for generating an X-ray image by processing an image composed of pixel values of the X-rays detected by the X-ray detector.

Although not disclosed in Japanese Unexamined Patent Application Publication No. 2020-195733, it is required that a predetermined site in which a lesion is likely to occur be clearly reflected in the acquired X-ray image when capturing an X-ray image of the subject. Such a predetermined site is of particular importance in diagnostics. However, depending on the predetermined site, it is not easy to assuredly include the predetermined site in the X-ray image. Therefore, the predetermined site may not be included in the imaging range in the acquired X-ray image.

Further, a radiological technician determines that a predetermined site does not overlap with the other sites based on the experience by confirming, for example, the posture of the subject when performing the X-ray imaging. Therefore, the correctness of the overlap between a predetermined site and the other site depends on the experience of the radiological technician. Consequently, in an inexperienced radiological technician, a predetermined site may not be sufficiently reflected in the acquired X-ray image due to the predetermined site being overlapped with the other site.

In these cases, the acquired X-ray image is determined to be a failed image (an image that cannot be used for diagnostics), and re-imaging is performed. Therefore, it is desired to suppress an increase in the exposure amount caused by re-capturing an X-ray image due to imaging failure by suppressing the occurrence of imaging failure of an X-ray image.

SUMMARY OF THE INVENTION

The present invention has been made to solve the above-described problems. An object of the present invention is to provide an X-ray imaging apparatus capable of suppressing an increase in the exposure amount caused by re-capturing an X-ray image due to imaging failure by suppressing the occurrence of imaging failure of an X-ray image.

In order to attain the above-described object, an X-ray imaging apparatus according to one aspect of the present invention is provided with:

an X-ray irradiation unit including an X-ray tube;
a detector configured to detect X-rays emitted from the X-ray irradiation unit;
an image generation unit configured to generate an X-ray image based on the X-rays detected by the detector;
an optical imaging unit configured to capture an optical image in a direction of a subject and the detector from a side of the X-ray irradiation unit;
a storage unit configured to store a trained model for outputting determination information for an input image based on the optical image including the subject imaged by the optical imaging unit, the determination information determining a state regarding an imaging range of a predetermined site of the subject or a relative position of the predetermined site to the other site of the subject;
a control unit configured to acquire the determination information, using the trained model; and
a notification unit configured to perform notification based on the determination information acquired by the control unit.

Here, the "optical image" denotes an image acquired by optically detecting visible light reflected by a subject.

In the X-ray imaging apparatus according to one aspect of the present invention, as described above, the control unit acquires the determination information using a trained model. The trained model is configured to, for the input image which is based on an optical image including the subject imaged by the optical imaging unit, output determination information. The determination information determines the imaging range of the predetermined site of the subject or the state regarding the relative position of the predetermined site to the other site.

By inputting the input image based on the optical image to the trained model to thereby acquire an output result, it is possible to determine whether the predetermined site of the subject is included within the imaging range in the X-ray image without confirming an X-ray image captured by actually emitting X-rays.

Further, by acquiring the output result, it is possible to determine whether the predetermined site of the subject does not overlap with the other site in the X-ray image without confirming an X-ray image captured by actually emitting X-rays and without relying on the experience of the radiological technician. Therefore, it is possible to suppress the occurrence of imaging failure of an X-ray image. As a consequence, by suppressing the occurrence of imaging failure of an X-ray image, it is possible to suppress an increase in the exposure amount caused by re-capturing of an X-ray image due to imaging failure.

BRIEF DESCRIPTION OF THE DRAWINGS

The preferred embodiments of the present invention are shown by way of example, and not limitation, in the accompanying figures.

DETAILED DESCRIPTION OF THE PREFERRED EMBODIMENTS

In the following paragraphs, some preferred embodiments of the present invention will be described by way of example and not limitation. It should be understood based on this disclosure that various other modifications can be made by those skilled in the art based on these illustrated embodiments.

Hereinafter, some embodiments in which the present invention is embodied will be described with reference to the attached drawings.

Figure 1:
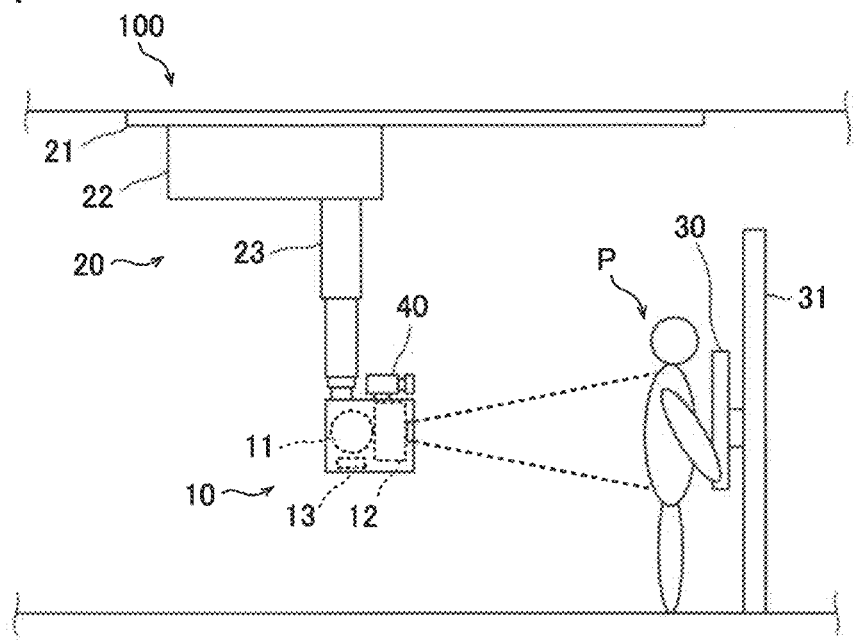
FIG. 1 is a schematic diagram showing the entire configuration of an X-ray imaging apparatus according to one embodiment.

With reference to FIG. 1, the configuration of an X-ray imaging apparatus 100 according to one embodiment will be described.

(Configuration of X-Ray Imaging Apparatus)

Figure 2:
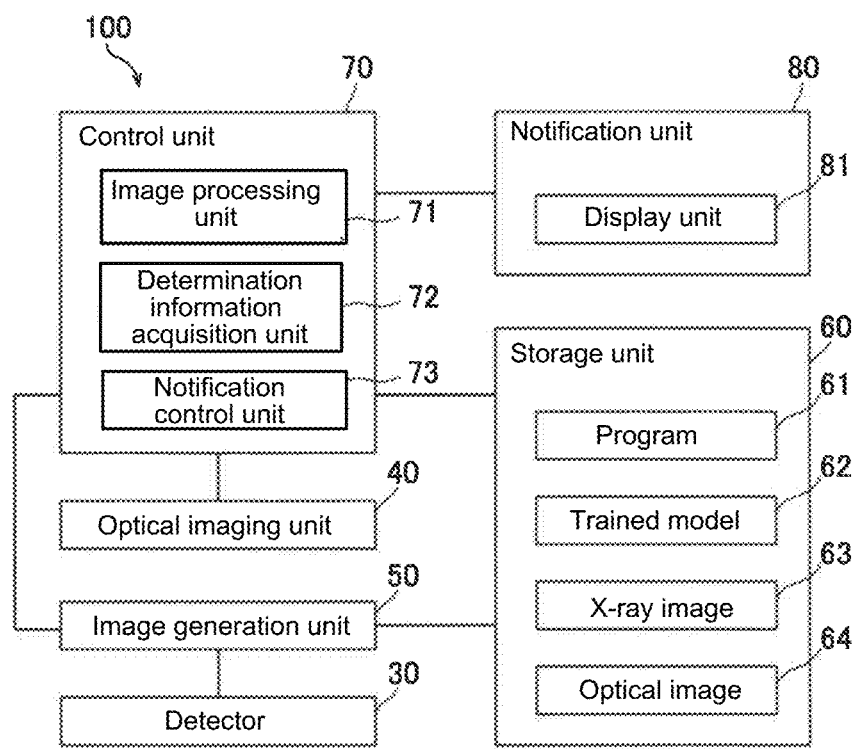
FIG. 2 is a block diagram of the X-ray imaging apparatus according to one embodiment.

The X-ray imaging apparatus 100 is provided with, as shown in FIG. 1 and FIG. 2, an X-ray irradiation unit 10, a moving mechanism 20, a detector 30, an optical imaging unit 40, an image generation unit 50 (see FIG. 2), a storage unit 60 (see FIG. 2), a control unit 70 (see FIG. 2), and a notification unit 80 (see FIG. 2).

The X-ray irradiation unit 10 includes an X-ray tube 11, a collimator 12, and a collimator lamp 13. The X-ray tube 11 is configured to irradiate a subject P with X-rays. The collimator 12 is configured to adjust the irradiation field 14 (see FIG. 4) of the X-rays emitted from the X-ray tube 11. The collimator 12 is provided in the vicinity of the X-ray tube 11 in the X-ray irradiation direction of the X-ray tube 11. The collimator 12 is provided with the collimator lamp 13. The collimator lamp 13 includes a light source of visible light. The X-ray irradiation field 14 can be confirmed by the visible light emitted from the collimator lamp 13 without using X-rays.

The moving mechanism 20 is configured to movably hold the X-ray irradiation unit 10. The moving mechanism 20 includes an overhead suspension 22 and a support portion 23. The moving mechanism 20 is supported by a rail 21 provided on the ceiling of the imaging room. The overhead suspension 22 is configured to be movable by the rail 21 in the horizontal direction. The overhead suspension 22 is configured to support the support portion 23. The support portion 23 is configured to support the X-ray irradiation unit 10. The support portion 23 is configured to be extendable and retractable in the vertical direction. The X-ray irradiation unit 10 is configured to be movable in the vertical direction by the support portion 23.

The detector 30 is configured to detect the X-rays emitted from the X-ray irradiation unit 10. The detector 30 includes, for example, an FPD (Flat Panel Detector). The detector 30 is attached to an imaging stand 31 for performing imaging in a posture (standing position) in which the subject P stands.

When performing X-ray imaging, the X-ray irradiation unit 10 is arranged at a position facing the detector 30 of the imaging stand 31 in the horizontal direction. The X-ray imaging apparatus 100 images the subject P standing in front of the imaging stand 31 between the X-ray tube 11 and the detector 30 facing in the horizontal direction.

The optical imaging unit 40 is configured to capture an optical image 64 (see FIG. 2). The optical imaging unit 40 includes an optical camera. The optical imaging unit 40 is mounted to the collimator 12. The optical imaging unit 40 is mounted to face the irradiation direction of the X-rays from the X-ray irradiation unit 10. The optical imaging unit 40 can capture the optical image in the direction of the subject P and the detector 30 from the side of the X-ray irradiation unit 10 when the X-ray irradiation unit 10 faces in the direction of the subject P and the detector 30. The optical image 64 captured by the optical imaging unit 40 is an image captured from substantially the same direction as the imaging direction of the X-ray image 63 (see FIG. 2). The optical imaging unit 40 continuously images the subject P at the time of capturing the X-ray image 63. The imaging range of the optical imaging unit 40 is set to include the range of the X-ray irradiation field 14 (see FIG. 4) and be larger than the range of the X-ray irradiation field 14.

As shown in FIG. 2, the image generation unit 50 is configured to generate the X-ray image 63 based on the X-rays detected by the detector 30. The image generation unit 50 includes, for example, a CPU (Central Processing Unit), an FPGA (Field-Programmable Gate Array), etc.

The storage unit 60 stores various programs 61 to be executed by the control unit 70. Further, the storage unit 60 stores a trained model 62, which will be described later. As will be described later, the trained model 62 includes a trained model 62a (see FIG. 3), a trained model 62b (see FIG. 5), and a trained model 62c (see FIG. 7). The storage unit 60 includes a non-volatile storage unit, such as, e.g., an HDD (Hard Disk Drive), or an SSD (Solid State Drive). The storage unit 60 is configured to store the X-ray image 63 generated by the image generation unit 50 and the optical image 64 captured by the optical imaging unit 40.

The control unit 70 is configured to acquire, using the trained model 62, determination information 65 (determination information 65a (see FIG. 3), determination information 65b (see FIG. 5), determination information 65c (see FIG. 7)) for determining the imaging range of the predetermined site of the subject P or the state regarding the relative position of the predetermined site to the other site.

Further, the control unit 70 is configured to control the notification unit 80 to perform notification based on the determination information 65. The control unit 70 is configured to generate a trained model input extraction image 67 (see FIG. 3) and a trained model input estimation image 68 (see FIG. 6). The control unit 70 includes a CPU (Central Processing Unit), a ROM (Read Only Memory), a RAM (Random Access Memory), a GPU (Graphics Processing Unit), or an FPGA (Field-Programmable Gate Array) configured for image processing.

The notification unit 80 is configured to perform notification based on the determination information 65 under the control of the control unit 70. The notification unit 80 includes a display unit 81 for displaying the information based on the determination information 65 acquired by the control unit 70. The display unit 81 is, for example, a liquid crystal device.

(Acquisition of Determination Information to Determine State Regarding Imaging Range of Apex Area of Lung of Subject)

Here, in capturing an X-ray image of the subject P, it is required that the acquired X-ray image 63 clearly reflect the predetermined site of the subject P. For example, when performing X-ray imaging of a chest, it is required that the lung field be clearly reflected in the acquired X-ray image. An apex area of a lung, which is an upper end of a lung (lung field) as an exemplary predetermined site, is the most common site of pulmonary tuberculosis. Therefore, an apex area of a lung is of particular importance in diagnostics. Therefore, an apex area of a lung needs to be clearly reflected in the acquired X-ray image.

Normally, the imaging region (X-ray irradiation field 14) of the X-ray image 63 of the chest is confirmed using the collimator lamp 13 mounted on the collimator 12. However, it is not easy to assuredly include the apex area of the lung in the X-ray image 63, and therefore, the apex area of the lung may not be sufficiently reflected in the acquired X-ray image 63. In this case, the acquired X-ray image 63 is determined to be a failed image, and re-imaging is performed. Therefore, it is required to suppress the occurrence of imaging failure of the acquired X-ray image 63.

Figure 3:
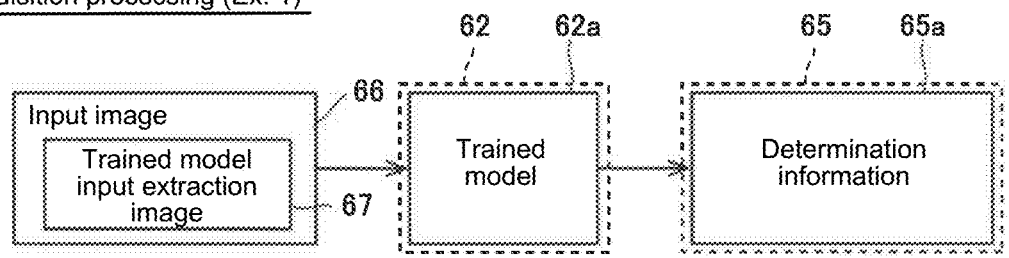
FIG. 3 is a diagram showing first exemplary determination information acquisition processing according to one embodiment.

Thus, as shown in FIG. 3 as Example 1, the control unit 70 is configured to acquire the determination information 65a using the trained model 62a. The determination information 65a indicates whether the apex of the lung of the subject P is included in the area of the X-ray irradiation field 14 based on the irradiation light from the collimator lamp 13 in the input image 66 and is used to determine the state regarding the imaging range of the apex of the lung as the predetermined site of the subject P.

Specifically, the control unit 70 generates a trained model input extraction image 67 in which the contour 95 of the subject P included in the optical image 64 captured by the optical imaging unit 40 and the X-ray irradiation field 14 are extracted. The control unit 70 is configured to input the trained model input extraction image 67, which is an input image 66, to the trained model 62 and then acquire the determination information 65a for determining the state regarding the imaging range of the apex area of the subject P, which is an output result.

(Trained Model Generation Method of Outputting Determination Information for Determining State Regarding Imaging Range of Apex Area of Lung of Subject)

Next, the generation method of a trained model 62a will be described. Note that the trained model 62a is generated by a computer (not shown). The computer includes a so-called personal computer and includes a processor and a storage unit. The computer can communicate with the X-ray imaging apparatus 100 over a network.

Figure 4:
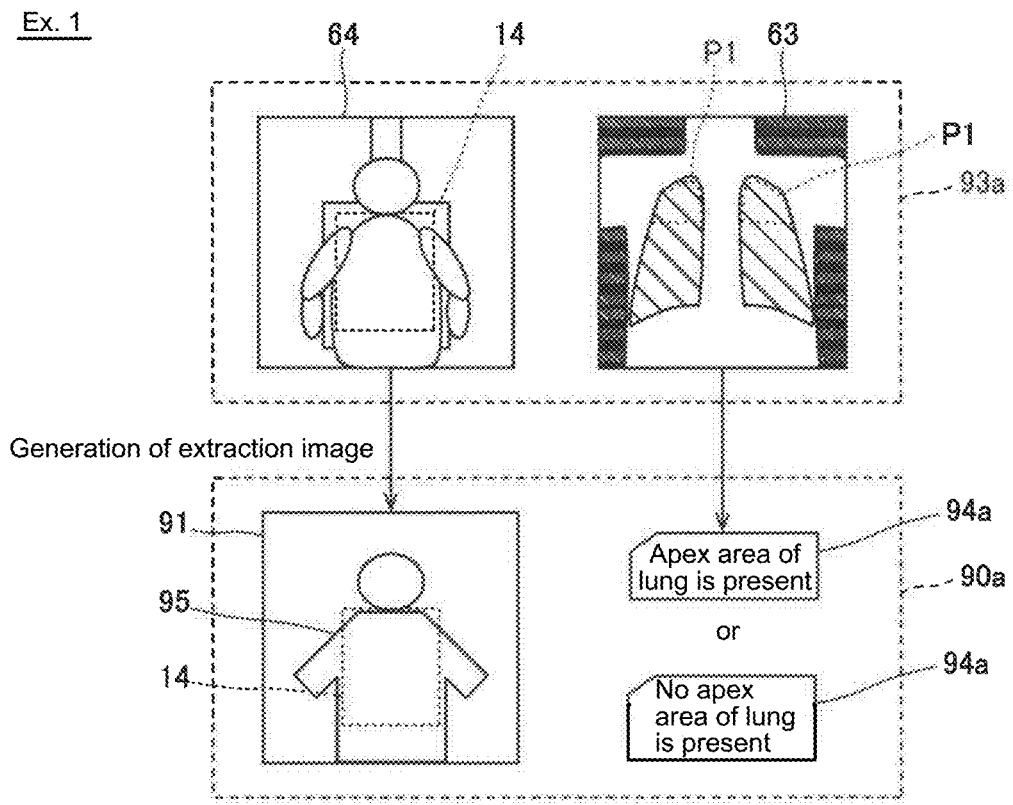
FIG. 4 is a diagram showing a first exemplary training dataset generation method according to one embodiment.

As shown in FIG. 4 as Example 1, a plurality of image sets 93a is acquired. Each image set 93a includes an X-ray image 63 in which a subject is reflected and an optical image 64 in which the subject imaged by an optical camera at the same time from substantially the same direction is reflected. The X-ray image 63 and the optical image 64 are images captured at the same time. Note that the image set 93a of the X-ray image 63 and the optical image 64 may be acquired by the X-ray imaging apparatus 100 according to this embodiment, or may be acquired by another X-ray imaging apparatus 100.

For the X-ray image 63 of the image set 93a, it is determined whether the apex area P1 of the lung is reflected. The determination of whether the apex area P1 of the lung is reflected in the X-ray image 63 may be performed visually by a doctor or may be performed by using a known image-recognition technique. The determination result of whether the apex area P1 of the lung is reflected in the X-ray image 63 is acquired as a label 94a of either "Apex area of lung is present" or "Apex area of lung is not present."

Conventionally, as an effort to reduce imaging failure, the protocol (procedure), the cause, the incidence rate, etc., in which imaging failure occurred in the past are subjected to statistical analysis processing, and the administrator analyzes them and instructs a radiological technician to reduce the incidence of imaging failure. Specifically, at the time when imaging failure is confirmed, the image generated based on the imaging failure is set as a failed image (specified as imaging failure), and the reason (reason of the imaging failure) is input by an input unit (not shown) of the X-ray imaging apparatus 100. The failed image (not shown) associated with the reason of the imaging failure is stored in the storage unit 60 (see FIG. 2).

For example, the failed image associated with the reason of the imaging failure of "No apex area of lung is present" stored in the storage unit 60 (see FIG. 2) may be used as an X-ray image 63 of "No apex area of lung is present" in the image set 93a. With this, the X-ray image 63 labeled as "No apex area of lung is present" can be easily acquired.

The optical image 64 of the image set 93a is subjected to the processing of extracting the contour 95 of the upper body of the subject and the irradiation range (X-ray irradiation field 14) of the visible light of the collimator lamp 13. The extraction of the contour 95 of the upper body of the subject and the irradiation range of the collimator lamp 13 is performed by using known techniques of human body posture analysis and image-recognition. The extraction processing for the optical image 64 generates a trained model generation extraction image 91 in which the contour 95 of the upper body of the subject and the frame of the X-ray irradiation field 14 are extracted. In the trained model generation extraction image 91, the X-ray irradiation field 14 in the contour 95 of the upper body of the subject is shown in a rectangular shape.

As described above, the training dataset 90a including the generated trained model generation extraction image 91 and the label 94a of the determination result of the X-ray image 63 is generated. A plurality of training datasets 90a is generated. The trained model 62a (see FIG. 3) is generated by performing machine learning using a plurality of generated training datasets 90a as training data. As the machine learning method of the trained model 62a, any arbitrary method, such as, e.g., a fully convolutional neural network (Fully Convolutional Networks: FCN), a neural network, a support vector machine (SVM), and boosting, can be used.

As shown in FIG. 3, the trained model 62a is stored in the storage unit 60 (see FIG. 2). The trained model 62a receives the input image 66 based on the optical image 64 captured by the optical imaging unit 40 and outputs the determination information 65a on the subject P (see FIG. 1) in the input image 66. The outputted determination information 65a is information indicating whether the apex area of the lung of the subject P is included in the area of the X-ray irradiation field 14 based on the irradiation light from the collimator lamp 13 in the input image 66.

(Acquisition of Determination Information to Determine State Regarding Relative Position of Apex Area of Lung to Clavicle of Subject)

Further, in order for the acquired X-ray image 63 to clearly capture the apex area of the lung as an exemplary predetermined site, it is required that the clavicle do not overlap with the apex area of the lung. A radiological technician empirically determines that a clavicle does not overlap with the apex area of the lung at the time of the X-ray imaging by checking the shoulder line 97 of the subject P. However, the correctness of the overlap between the apex area of the lung and the clavicle depends on the experience of the radiological technician, and therefore, the apex area of the lung may not be sufficiently reflected due to the overlap between the clavicle and the lung in the acquired X-ray image 63. In this case, the acquired X-ray image 63 is determined to be a failed image, and re-imaging is performed. Therefore, it is required to suppress the occurrence of imaging failure of the acquired X-ray image 63.

Figure 5:
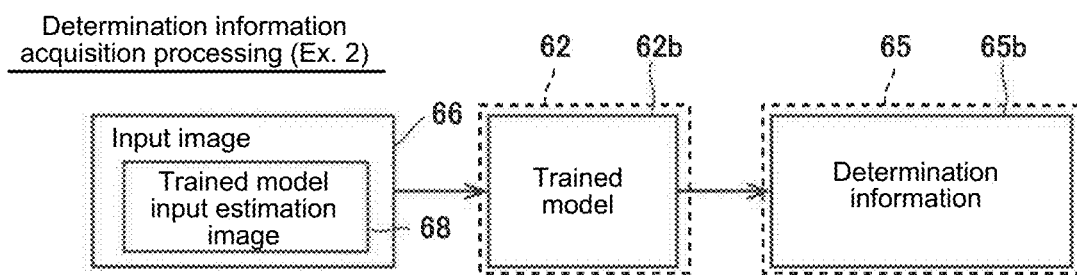
FIG. 5 is a diagram showing second exemplary determination information acquisition processing according to one embodiment.

Thus, as shown in FIG. 5 as Example 2, the control unit 70 is configured to acquire determination information 65b using a trained model 62b. The determination information 65b indicates whether the apex area of the lung of the subject P and the clavicle overlap with each other in the input image 66 and is used to determine the state regarding the relative position of the apex of the lung of the subject P as the predetermined site to the clavicle as the other site. Hereinafter, the difference from the above-described acquisition of the determination information 65a will be described.

Specifically, the control unit 70 generates a trained model input estimation image 68 in which the shoulder line 97 (see FIG. 6) of the subject P included in the optical image 64 captured by the optical imaging unit 40 is estimated. The control unit 70 is configured to input the trained model input estimation image 68, which is an input image 66, to the trained model 62b and acquire the determination information 65b for determining the state regarding the relative position of the apex area of the lung to the clavicle.

(Trained Model Generation Method of Outputting Determination Information to Determine State Regarding Relative Position of Apex Area of Lung to Clavicle)

Figure 6:
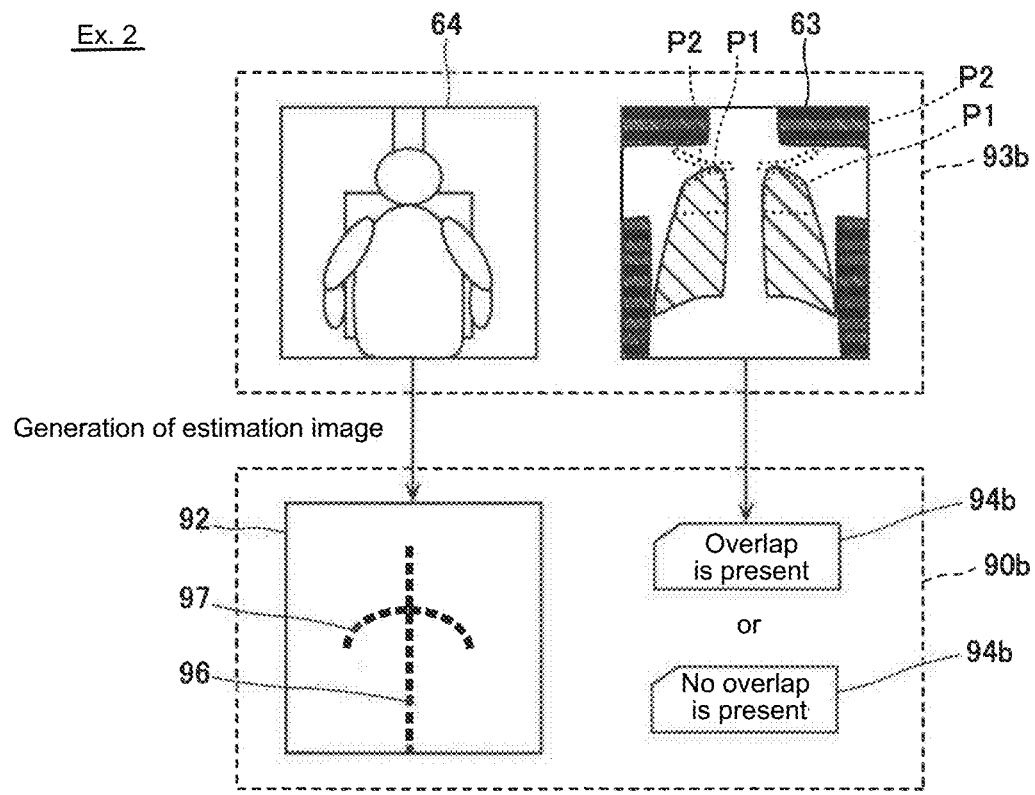
FIG. 6 is a diagram showing a second exemplary training dataset generation method according to one embodiment.

As shown in FIG. 6 as Example 2, in the same manner as the above-described generation method of the trained model 62a, a plurality of image sets 93b including the X-ray image 63 and the optical image 64 is acquired. For the X-ray image 63 of the image set 93b, it is determined whether the apex area P1 of the lung and the clavicle P2 overlap with each other. The determination result of whether the apex area P1 of the lung and the clavicle P2 overlap with each other in the X-ray image 63 is acquired as a label 94b of either "No overlap between the apex area of the lung and the clavicle is present" or "Overlap between the apex area of the lung and the clavicle is present."

The optical image 64 of the image set 93b is subjected to the processing of estimating the shoulder line 97 of the subject. The estimation of the shoulder line 97 of the subject is performed by using a known technique of human body posture analysis and image-recognition. By performing the estimation processing on the optical image 64, a trained model generation estimation image 92 in which the center line 96 of the subject based on the backbone and the shoulder line 97 are estimated is generated. In the trained model generation estimation image 92 shows the center line 96 of the subject P based on the backbone and the shoulder line 97 of the subject P.

As described above, the training dataset 90b including the generated trained model generation estimation image 92 and the label 94b of the determination result of the X-ray image 63 is generated. The trained model 62b (see FIG. 5) is generated by performing machine learning using a plurality of generated training datasets 90b as training data. The generated trained model 62b is stored in the storage unit 60. The trained model 62b receives an input image 66 based on the optical image 64 captured by the optical imaging unit 40 and outputs the determination information 65b on the subject P in the input image 66. The determination information 65b to be outputted is information indicating whether the apex area of the lung and the clavicle of the subject P overlap with each other in the input image 66.

(Acquisition of Determination Information to Determine State Regarding Relative Position of Lung Field to Scapula of Subject)

Further, in order for the acquired X-ray image 63 to clearly reflect the lung field as an exemplary predetermined site, it is required that the scapula do not overlap with the lung field. A radiological technician empirically determines that a scapula does not overlap with a lung field at the time of X-ray imaging by checking the internal rotation of the arm of the subject P. Here, the term "internal rotation" refers to a motion of rotating the upper arm or the thigh toward the inside of the body without changing the position.

However, the correctness of the overlap between a lung field and a scapula depends on the experience of the radiological technician, and therefore, the lung field may not be sufficiently reflected in the acquired X-ray image 63 due to the overlap between the scapula and the lung field in the acquired X-ray image 63. In this case, the acquired X-ray image 63 is determined to be a failed image, and re-imaging is performed. Therefore, it is required to suppress the occurrence of imaging failure of the acquired X-ray image 63.

Figure 7:
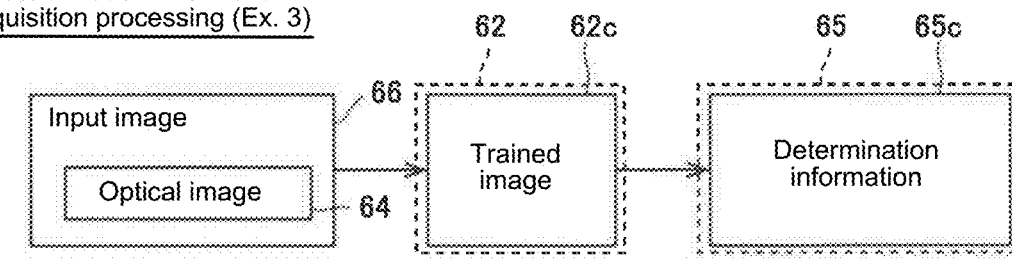
FIG. 7 is a diagram showing third exemplary determination information acquisition processing according to one embodiment.

Thus, as shown in FIG. 7 as Example 3, the control unit 70 is configured to acquire determination information 65c using the trained model 62c. The determination information 65c indicates whether the lung field and the scapula of the subject P overlap with each other in the input image 66 and is used to determine the state regarding the relative position of the lung field of the subject P as the predetermined site to the scapula as the other site. Hereinafter, the difference from the above-described acquisition of the determination information 65a will be described.

Specifically, the control unit 70 is configured to input the optical image 64 captured by the optical imaging unit 40 as an input image 66 to the trained model 62c and acquire the determination information 65c as an output result for determining the state regarding the relative position of the lung field of the subject P to the scapula.

(Trained Model Generation Method to Output Determination Information to Determine State Regarding Relative Position of Lung Field to Scapula of Subject)

Figure 8:
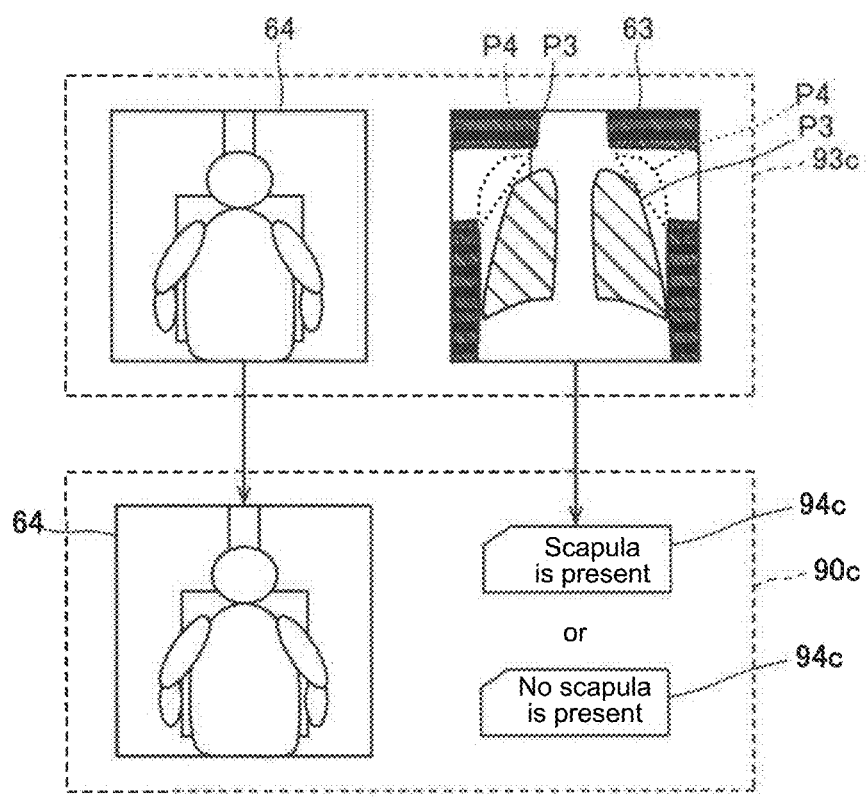
FIG. 8 is a diagram showing a third exemplary training dataset generation method according to one embodiment.

As shown in FIG. 8 as Example 3, a plurality of image sets 93c including an X-ray image 63 and an optical image 64 is acquired. For the X-ray image 63 of the image set 93c, it is determined whether the lung field P3 and the scapula P4 overlap with each other. The determination of whether the lung field P3 and the scapula P4 overlap with each other in the X-ray image 63 is acquired as a label 94c of either "No scapula is present" or "Scapula is present."

In the generation of the trained model 62c, unlike the generation of the trained model 62a described above, the generation of the extraction image based on the optical image 64 of the image set 93c is not performed. As described above, the training dataset 90c including the optical image 64 and the label 94c of the determination result of the X-ray image 63 is generated.

The trained model 62c is generated by performing machine learning using a plurality of generated training datasets 90c as training data. The generated trained model 62c is stored in the storage unit 60. The trained model 62c receives an input image 66, which is an optical image 64 captured by the optical imaging unit 40, and outputs determination information 65c of the subject P in the input image 66. The determination information 65c to be outputted is information indicating whether the lung field and the scapula of the subject P overlap with each other in the input image 66.

(Functional Block of Control Unit)

With reference to FIG. 2, the functional block included in the control unit 70 will be described. The control unit 70 composed of a CPU or the like as hardware includes, as a functional block of software (program 61), an image processing unit 71, a determination information acquisition unit 72, and a notification control unit 73. The control unit 70 functions as the image processing unit 71, the determination information acquisition unit 72, and the notification control unit 73 by executing the programs 61 stored in the storage unit 60. The image processing unit 71, the determination information acquisition unit 72, and the notification control unit 73 may be individually configured by hardware with a dedicated processor (processing circuit).

The image processing unit 71 is configured to generate a trained model input extraction image 67 in which the contour 95 of the subject P (see FIG. 1) included in the optical image 64 captured by the optical imaging unit 40 and the irradiation range (X-ray irradiation field 14) of the visible light of the collimator lamp 13 are extracted. The image processing by the image processing unit 71 is performed by the same method as the image processing in the generation method of the trained model 62a described above, and therefore, the explanation thereof will be omitted.

The image processing unit 71 generates a trained model input extraction image 67, which is the same as the trained model generation extraction image 91 (see FIG. 4), in which the irradiation field 14 of the X-rays in the contour 95 of the upper body of the subject P is shown in a rectangular shape. The trained model input extraction image 67 generated by the image processing unit 71 is an input image 66 (see FIG. 3) to be inputted to the trained model 62a.

Further, the image processing unit 71 is configured to generate a trained model input estimation image 68 (see FIG. 5) in which the shoulder line 97 of the subject P included in the optical image 64 captured by the optical imaging unit 40 is estimated.

The image processing unit 71 generates a trained model input estimation image 68, which is the same as the trained model generation estimation image 92 (see FIG. 6), in which the center line 96 of the subject P based on the backbone and the shoulder line 97 of the subject P are shown by dashed lines. The trained model input estimation image 68 generated by the image processing unit 71 is an input image 66 (see FIG. 5) to be inputted to the trained model 62b.

As shown in FIG. 3, the determination information acquisition unit 72 is configured to input the trained model input extraction image 67 generated by the image processing unit 71 and acquire the determination information 65a on the subject P, which is an output result, using the trained model 62a. As shown in FIG. 5, the determination information acquisition unit 72 is configured, using the trained model 62b, to input the trained model input estimation image 68 generated by the image processing unit 71 as an input image 66 and acquire the determination information 65b on the subject P as an output result. Further, as shown in FIG. 7, the determination information acquisition unit 72 is configured, using the trained model 62c, to input the optical image 64 captured by the optical imaging unit 40 as an input image 66 and acquire the determination information 65c of the subject P, which is an output result.

As shown in FIG. 2, the notification control unit 73 is configured to cause the notification unit 80 to perform notification based on the determination information 65a on the subject P, which is the acquired output result. In a case where the determination information 65a on the subject P is "Apex area of lung is present," the notification control unit 73 is configured to cause the notification unit 80 to display the characters of "Apex area of lung is present" on the display unit 81. Further, in a case where the determination information 65a on the subject P is "No apex area of lung is present," the notification control unit 73 is configured to cause the notification unit 80 to display, for example, the characters of "No apex area of lung is present" on the display unit 81.

Further, the notification control unit 73 is configured to cause the notification unit 80 to perform notification based on the determination information 65b on the subject P, which is the acquired output result.

In a case where the determination information 65b on the subject P is "No-overlap between the apex area of the lung and the clavicle is present," the notification control unit 73 is configured to cause the display unit 81 of the notification unit 80 to display, for example, the characters of "No overlap between the apex area of the lung and the clavicle." Further, in a case where the determination information 65b on the subject P is "Overlap between the apex area of the lung and the clavicle is present," the notification control unit 73 is configured to cause the display unit 81 of the notification unit 80 to display, for example, the characters of "Overlap between the apex area of the lung and the clavicle is present."

Further, the notification control unit 73 is configured to cause the notification unit 80 to perform notification based on the determination information 65c on the subject P, which is the acquired output result. In a case where the determination information 65c on the subject P is "No scapula is present," the notification control unit 73 is configured to cause the display unit 81 of the notification unit 80 to display, for example, the characters of "No scapula is present." Further, in a case where the determination information 65c on the subject is "Scapula is present," the notification control unit 73 is configured to cause the display unit of the notification unit 80 to display, for example, the characters of "Scapula is present."

Note that the notification control unit 73 may be configured to cause the notification unit 80 to output the above-described contents by voice. Further, in a case where the determination information 65a on the subject P is "Apex area of lung is present," the determination information 65b on the subject P is "No overlap between the apex area of the lung and the clavicle," and the determination information 65c on the subject P is "no scapula is present," the notification control unit 73 may be configured to cause the display unit 81 of the notification unit 80 to display the characters of "Image-capturing enabled state."

(Acquisition Processing of Determination Information)

Figure 9:
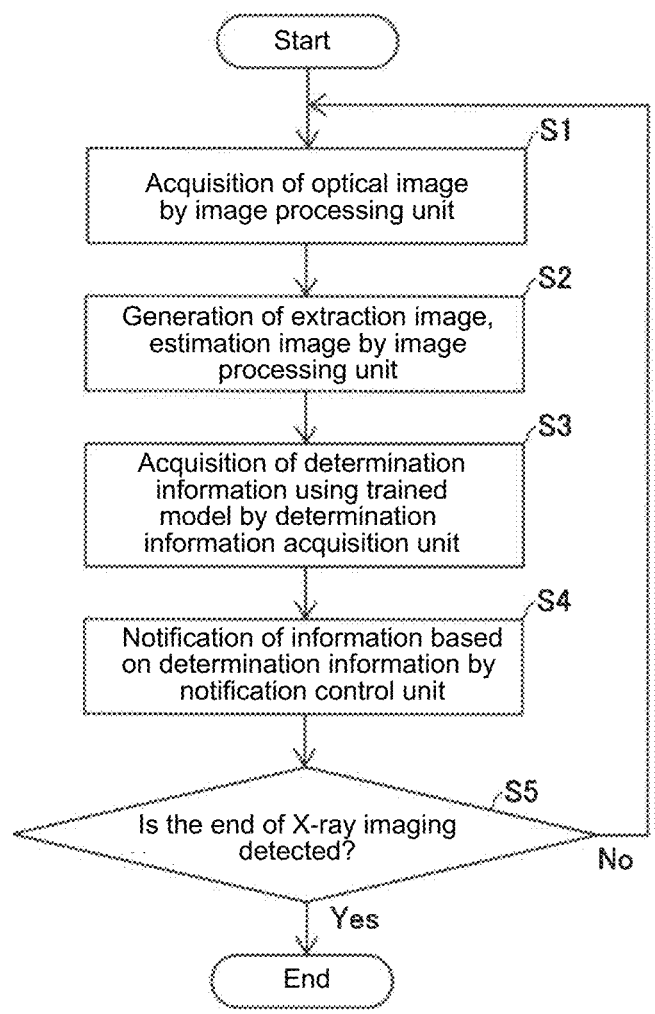
FIG. 9 is a flowchart for explaining acquisition processing of determination information according to one embodiment.

With reference to FIG. 9, the acquisition processing of the determination information 65a to 65c according to this embodiment will be described. Note that the acquisition processing of the determination information 65a to 65c, which will be described below, is executed by the control unit 70 including a CPU as hardware.

In Step S1, the image processing unit 71 (control unit 70) acquires the optical image 64 captured by the optical imaging unit 40. Thereafter, the processing proceeds to Step S2.

In Step S2, the image processing unit 71 (control unit 70) generates the trained model input extraction image 67 and the trained model input estimation image 68 based on the acquired optical image 64. Thereafter, the processing proceeds to Step S3.

In Step S3, using the trained model 62a, the determination information acquisition unit 72 (control unit 70) inputs the trained model input extraction image 67 generated by the image processing unit 71 as an input image 66 and acquires the determination information 65a, which is an output result. Further, using the trained model 62b, the determination information acquisition unit 72 (control unit 70) acquires the determination information 65b, which is an output result, by inputting the trained model input estimation image 68 generated by the image processing unit 71 as an input image 66. Further, using the trained model 62c, the determination information acquisition unit 72 (control unit 70) inputs the optical image 64 captured by the optical imaging unit 40 as an input image 66 and acquires the determination information 65c, which is an output result. Thereafter, the processing proceeds to Step S4.

In Step S4, the notification control unit 73 causes the notification unit 80 to notify the information based on the determination information 65a to 65c on the subject P, which is the acquired output result. Thereafter, the processing proceeds to Step S5.

In Step S5, in a case where the control unit 70 has detected the end of capturing the X-ray image 63 by the radiological technician (Yes in Step S4), the processing ends, and in a case where the control unit 70 has not detected the end of capturing the X-ray image 63 by the radiological technician (No in Step S5), the processing returns to Step S1.

In a case where the imaging range of the predetermined site of the subject S or the state regarding the relative position of the predetermined site to the other site is determined to be appropriate in the determination information 65a to 65c by the notification of the information based on the determination information 65a to 65c of the subject P by the notification unit 80, the radiological technician can capture the X-ray image 63 by emitting X-rays. Further, in a case where the imaging range of the predetermined site of the subject P or the state regarding the relative position of the predetermined site to the other site is determined not to be appropriate in the determination information 65a to 65c, the radiological technician can change the posture of the subject P without emitting X-rays. As a consequence, it is possible to more appropriately suppress the occurrence of imaging failure of the X-ray image 63.

Effects of this Embodiment

In this embodiment, the following effects can be obtained.

In this embodiment, as described above, the X-ray imaging apparatus 100 is provided with: the X-ray irradiation unit 10 including the X-ray tube 11; the detector 30 for detecting the X-rays emitted from the X-ray irradiation unit 10; the image generation unit 50 for generating the X-ray image 63 based on the X-rays detected by the detector 30; the optical imaging unit 40 for capturing the optical image 64 in the direction of the subject P and the detector 30 from the X-ray irradiation unit 10 side; the storage unit 60 for storing the trained model 62a to 62c that outputs the determination information 65a to 65c for determining the imaging range of the predetermined site of the subject P and the state regarding the relative position of the predetermined side to the other site to the input image 66 generated based on the optical image 64 including the subject P captured by the optical imaging unit 40; the determination information acquisition unit 72 for acquiring the determination information 65a to 65c by using the trained model 62a to 62c; and the notification unit 80 for performing the notification based on the determination information 65a to 65c acquired by the determination information acquisition unit 72.

By inputting the input image 66 generated based on the optical image 64 into the trained model 62a to 62c and acquiring the output result, it is possible to determine whether the predetermined site of the subject P is included in the imaging range in the X-ray image without confirming the X-ray image 63 captured by actually irradiating X-rays. Further, by acquiring the output result, it is possible to determine whether the predetermined site of the subject P is sufficiently reflected in the X-ray image by not being overlapped with the other site in the X-ray image without confirming an X-ray image actually captured by emitting X-rays and without relying on the experience of the radiological technician. Therefore, it is possible to suppress the occurrence of imaging failure of the X-ray image 63. As a consequence, by suppressing the occurrence of imaging failure of the X-ray image 63, it is possible to suppress the increase in the exposure amount caused by re-capturing the X-ray image 63 due to the imaging failure.

Further, in this embodiment, as described above, the trained models 62a to 62c are configured to receive the input image 66 generated based on the optical image 64 captured by the optical imaging unit 40 from substantially the same direction as the imaging direction of the X-ray image 63 and output the determination information 65a to 65c on the subject P in the input image 66. The determination information acquisition unit 72 is configured to acquire the determination information 65a to 65c in the input image 66 using the trained models 62a to 62c before emitting the X-rays to capture the X-ray image 63.

With this, by inputting the input image 66 generated based on the optical image 64 captured by the optical imaging unit 40 from substantially the same direction as the imaging direction of the X-ray image 63 to the trained model 62a to 62c and acquiring the output result, before emitting X-rays to capture the X-ray image 63, it is possible to determine whether the imaging range of the predetermined site of the subject P or the state regarding the relative position of the predetermined site to the other site is appropriate. Therefore, it is possible to further suppress the occurrence of imaging failure of the X-ray image 63. As a result, by further suppressing the occurrence of imaging failure of the X-ray image 63, it is possible to suppress the increase in the exposure amount caused by the re-capturing of the X-ray image 63 due to the imaging failure.

Further, in this embodiment, as described above, the determination information acquisition unit 72 is configured to acquire the determination information 65a for determining the state regarding the imaging range of the apex area of the lung of the subject P outputted from the trained model 62a, the determination information 65b for determining the status regarding the relative position of the apex of the lung of the subject P outputted from the trained model 62b to the clavicle, or the determination information 65c for determining the state regarding the relative position of the scapula of the subject P outputted from the trained model 62c to the lung field.

With this, the radiological technician can capture the X-ray image 63 based on the acquired determination information 65a to 65c. As a consequence, it is possible to suppress that the apex area of the lung or the lung field is not sufficiently reflected in the acquired X-ray image 63, and therefore, the occurrence of imaging failure of the X-ray image 63 can be accurately and appropriately suppressed.

Further, in this embodiment, as described above, the X-ray irradiation unit 10 includes the collimator 12 for defining the X-ray irradiation field 14 and the collimator lamp 13 for making the X-ray irradiation field 14 visible. The determination information acquisition unit 72 is configured to acquire the determination information 65a for determining the state regarding the imaging range of the apex of the lung of the subject P as the predetermined site using the trained model 62a. The determination information 65a indicates whether the apex of the lung of the subject P is included in the area of the X-ray irradiation field 14 based on the optical light from the collimator lamp 13 in the input image.

With this, it is possible to acquire the determination information 65a indicating whether the apex area of the lung of the subject P is included in the area of the X-ray irradiation field 14 based on the irradiation light from the collimator lamp 13 in the input image 66.

Therefore, in a case where it is determined that the apex area of the lung of the subject P is included in the determination information 65a, the radiological technician can capture the X-ray image 63 by emitting X-rays. Further, in a case where it is determined in the determination information 65a that the apex area of the lung of the subject P is not included, the radiological technician can move the subject P or move the position of the X-ray irradiation unit 10 and that of the detector 30 without emitting X-rays. As a consequence, it is possible to more appropriately suppress the occurrence of imaging failure of the X-ray image 63.

Further, in this embodiment, as described above, the determination information acquisition unit 72 is configured to generate the trained model input extraction image 67 in which the contour 95 of the subject P and the X-ray irradiation field 14 included in the optical image 64 captured by the optical imaging unit 40 are extracted, input the trained model input extraction image 67, which is the input image 66, to the trained model 62a, and acquire the determination information 65a on the subject P, which is an output result.

With this, the trained model 62a uses the trained model input extraction image 67 in which the contour 95 of the subject and the X-ray irradiation field 14 are extracted as the input image 66, and therefore, as compared with the case where the optical image 64 captured by the optical imaging unit 40 is used as the input image 66, it is possible to improve the accuracy of the determination information 65a, which is an output result.

Further, in this embodiment, as described above, the determination information acquisition unit 72 is configured to acquire, using the trained model 62b, the determination information 65b for determining the state regarding the relative position of the apex area of the lung of the subject P as the predetermined site to the clavicle as the other site. The determination information 65b indicates whether the apex area of the lung of the subject and the clavicle overlap with each other in the input image 66.

With this, it is possible to acquire the determination information 65b indicating whether the apex area of the lung of the subject P and the clavicle overlap with each other in the input image 66. Therefore, in a case where it is determined in the determination information 65b that the apex area of the lung of the subject P and the clavicle do not overlap with each other, the radiological technician can capture the X-ray image 63 by emitting X-rays. Further, in a case where it is determined that the apex area of the lung and the clavicle of the subject P overlap with each other, the radiological technician can change the posture of the subject P without emitting X-rays. Consequently, it is possible to more appropriately suppress the occurrence of imaging failure of the X-ray image 63 and the increase in the exposure amount caused by re-imaging.

Further, in this embodiment, as described above, the determination information acquisition unit 72 is configured to generate the trained model input estimation image 68 in which the the shoulder line 97 of the subject P included in the optical image 64 captured by the optical imaging unit 40 is estimated, input the estimated trained model input estimation image 68, which is an input image 66, to the trained model 62b, and acquire the determination information 65b on the subject P, which is an output result.

With this, the trained model 62b uses, as the input image 66, the trained model input estimation image 68 in which shoulder line 97 of the subject P is estimated, and therefore, it is possible to improve the accuracy of the determination information 65b, which is an output result, as compared with the case where the optical image 64 captured by the optical imaging unit 40 is used as the input image 66.

Further, in this embodiment, as described above, the determination information acquisition unit 72 is configured to acquire the determination information 65c using the trained model 62c. The determination information 65c indicates whether the lung field and the scapula of the subject P overlap with each other in the input image 66 and determines the state regarding the relative position of the lung field of the subject P as the predetermined site to the scapula as the other site.

With this, it is possible to acquire the determination information 65c indicating whether the lung field and the scapula of the subject P overlap with each other in the input image 66.

Therefore, in a case where it is determined in the determination information 65c that the lung field and the scapula of the subject P do not overlap with each other, the radiological technician can capture the X-ray image 63 by emitting X-rays. Further, in a case where it is determined in the determination information 65c that the lung field and the scapula of the subject P overlap with each other, the radiological technician changes the posture of the subject P without emitting X-rays. As a result, it is possible to more appropriately suppress the occurrence of imaging failure of the X-ray image 63 and the increase in the exposure amount caused by re-imaging.

Further, in this embodiment, as described above, the optical imaging unit 40 is attached to the collimator 12 for defining the X-ray irradiation field 14, included in the X-ray irradiation unit 10. With this, the optical imaging unit 40 can capture the optical image 64 from substantially the same direction as the imaging direction of the X-ray image 63, so that the accuracy of the determination information 65 as an output result can be further improved.

Further, in this embodiment, as described above, the notification unit 80 includes the display unit 81 for displaying the information based on the determination information 65a to 65c acquired by the determination information acquisition unit 72. With this, the radiological technician can easily visually recognize the determination information 65a to 65c, so that it is possible to more appropriately suppress the occurrence of imaging failure of the X-ray image 63.

[Modifications]

It should be understood that the embodiments disclosed here are examples in all respects and are not restrictive. The scope of the present invention is shown by claims rather than the descriptions of the embodiments described above, and includes all changes (modifications) within the meaning and the scope equivalent to the claims.

For example, in the above-described embodiment, an example is shown in which the control unit 70 is configured to acquire the determination information 65a, the determination information 65b, and the determination information 65c, but the present invention is not limited thereto. For example, the control unit 70 may be configured to acquire the determination information 65a and the determination information 65b but not acquire the determination information 65c. Further, the control unit 70 may be configured to acquire the determination information 65a and the determination information 65c but not to acquire the determination information 65b. Further, the control unit 70 may be configured to acquire the determination information 65b and the determination information 65c but not to acquire the determination information 65a. The control unit 70 may be configured to acquire the determination information 65a but not acquire the determination information 65b and the determination information 65c. The control unit 70 may be configured to acquire the determination information 65b but not acquire the determination information 65a and the determination information 65c. The control unit 70 may be configured to acquire the determination information 65c but not acquire the determination information 65a and the determination information 65b.

Figure 10:
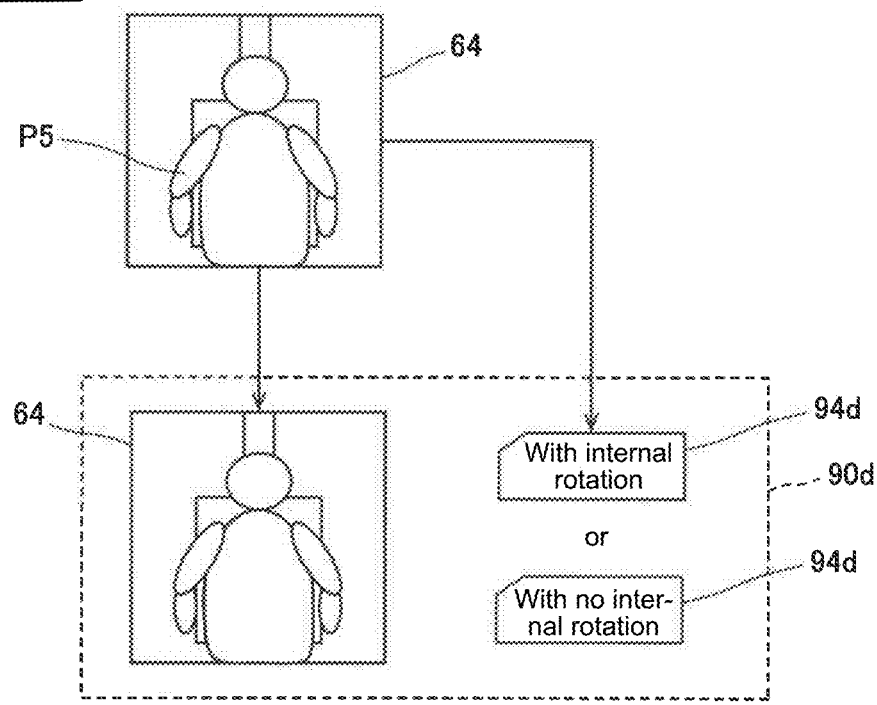
FIG. 10 is a diagram showing a training dataset generation method according to Modification 1.

Further, in the above-described embodiment related to the acquisition of the determination information 65c, an example is shown in which the training dataset 90c including the optical image 64 and the label 94 of the determination result of the X-ray image 63 is generated, but the present invention is not limited thereto. As shown in shown in FIG. 10 as Modification 1, the training dataset 90d may include the optical image 64 and the label 94d of the determination result of the optical image 64.

In this case, for example, a plurality of optical images 64 reflecting the subject captured from substantially the same direction as the imaging direction of the X-ray image 63 is acquired. For the acquired optical image 64, it is determined whether the arm P5 of the subject is sufficiently internally rotated. In the optical image 64, the determination of whether the arm P5 of the subject is sufficiently internally rotated is acquired as the label 94d of either "With internal rotation" or "Without internal rotation." As described above, the training dataset 90d including the optical image 64 and the label 94d of the determination result of the optical image 64 is generated.

The trained model 62 is generated by performing machine learning using a plurality of generated training datasets 90d as training data. The generated trained model 62 is stored in the storage unit 60. The trained model 62 receives the input image 66, which is the optical image 64 captured by the optical imaging unit 40, and outputs the determination information 65 on the subject P in the input image 66. The determination information 65 to be outputted is the information indicating whether the arm of the subject P is internally rotated in the input image 66.

Using the trained model 62, the determination information acquisition unit 72 is configured to input the optical image 64 captured by the optical imaging unit 40 as the input image 66 and acquire the determination information 65 on subject P, which is an output result.

The notification control unit 73 is configured to cause the notification unit 80 to perform notification based on the determination information on the subject P, which is the acquired output result. In a case where the determination information 65 on the subject P is "With internal rotation," the notification control unit 73 is configured to cause the display unit 81 of the notification unit 80 to display the characters of "With internal rotation." Further, in a case where the determination information 65 on the subject P is "With no internal rotation," the notification control unit 73 is configured to cause the display unit 81 of the notification unit 80 to display the characters of "With no internal rotation."

In Modification 1, the determination information acquisition unit 72 is configured to acquire the determination information 65 outputted from the trained model 62 for determining the state of the internal rotation of the arm of the subject P serving an index of the overlap between the lung field and the scapula of the subject P. With this, the radiological technician can capture the X-ray image 63 based on the acquired determination information 65. Consequently, it is possible to suppress that the lung field is not sufficiently reflected due to the overlap between the lung field and the scapula in the acquired X-ray image 63, and therefore, it is possible to accurately and appropriately suppress the occurrence of imaging failure of the X-ray image 63.

Further, in Modification 1, using the trained model 62, the determination information acquisition unit 72 is configured to acquire the status information on the internal rotation of the arm as an index of the subject P, in which it is indicated whether the arm of the subject P is rotated toward the inside of the body in the input image 66.

With this, it is possible to acquire the determination information indicating whether the arm of the subject P is rotated toward the inside of the body in the input image 66. Therefore, in a case where it is determined in the determination information 65 that the arm of the subject P is internally rotated, the radiological technician can capture the X-ray image 63 by emitting X-rays. In a case where it is determined in the determination information 65 that the arm of the subject P is not internally rotated, the radiological technician can change the posture of the subject P without emitting X-rays. As a result, it is possible to more appropriately suppress the occurrence of imaging failure of the X-ray image 63.

Further, in the above-described embodiment related to the acquisition of the determination information 65c, an example is shown in which the extraction processing or the estimation processing is not performed on the optical image of the image set 93c when generating the trained model 62, and the generation of the extraction image or the estimation image based on the optical image 64 captured by the optical imaging unit 40 by the image processing unit 71 is not performed, but the present invention is not limited thereto.

Figure 11:
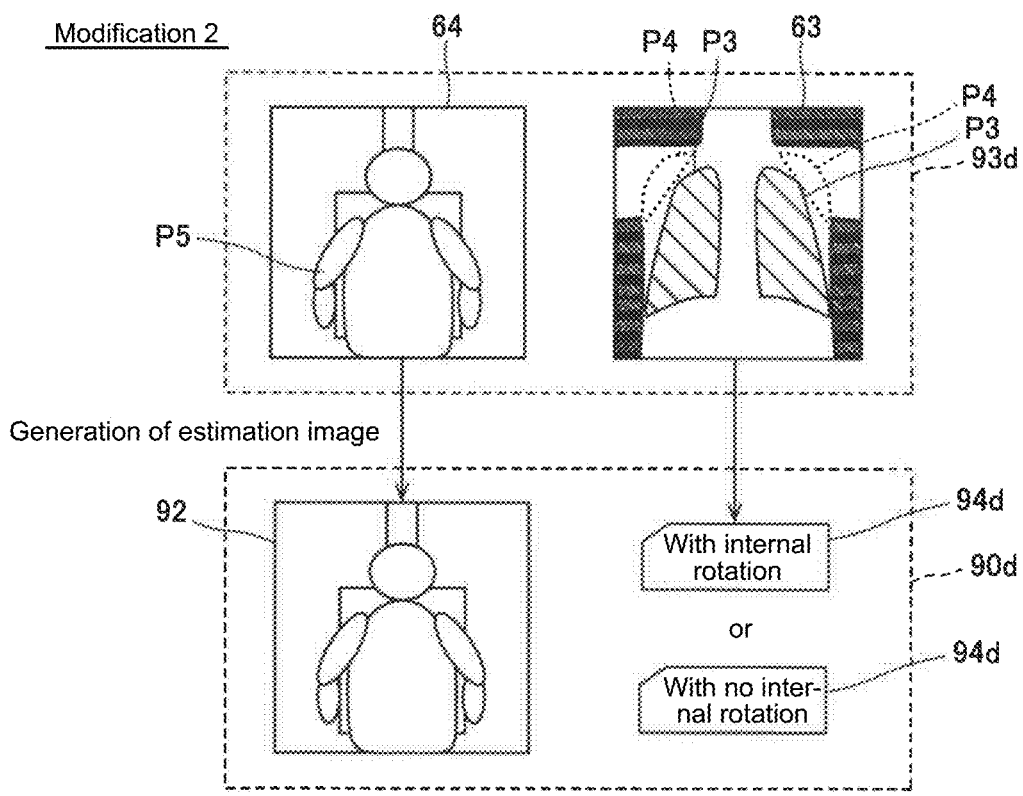
FIG. 11 is a diagram showing a training dataset generation method according to Modification 2.

For example, like Modification 2 shown in FIG. 11, it may be configured such that when generating the trained model 62, processing of estimating the internal rotation state of the arm P5 of the subject P to the optical image 64 of the image set 93d is performed to generate the trained model input estimation image 68 in which the internal rotation of the arm of the subject P included in the optical image 64 captured by the optical imaging unit 40 by the image processing unit 71.

That is, the control unit 70 may be configured to generate the trained model input estimation image 68 in which the internal rotation state of the arm of the subject P included in the optical image 64 captured by the optical imaging unit 40 is estimated, input the trained model input estimation image 68, which is the input image 66, to the trained model 62, and acquire the determination information 65 of the subject P, which is an output result.

With this, the trained model 62 uses, as the input image 66, the trained model input estimation image 68 in which the internal rotation status of the arm of the subject P is estimated, so that it is possible to improve the accuracy of the determination information, which is an output result, as compared with the case where the optical image 64 captured by the optical imaging unit 40 is used as the input image 66.

Further, in the above-described embodiment, an example is shown in which the extraction processing or the estimation processing is performed on the optical image 64 of the image set 93 when generating the trained model 62a, 62b, and the generation of the trained model input extraction image 67 or the trained model input estimation image 68 based on the optical image 64 captured by the optical imaging unit 40 by the image processing unit 71 is performed, but the present invention is not limited thereto.

For example, in the above-described embodiment, it may be configured such that when generating the trained model 62a, 62b, the extraction processing or the estimation processing is not performed on the optical image 64 of the image set 93a, 93b, and the trained model 62 may be generated using the optical image 64 and the training dataset 90 including the label 94a, 94b of the determination result of the X-ray image 63.

Further, in the above-described embodiment, the control unit 70 may be configured to, using the trained model 62a, 62b, input the optical image 64 captured by the optical imaging unit 40 as the input image 66 and acquire the determination information 65a, 65b of the subject P, which is an output result.

Further, in the above-described embodiment, an example is shown in which the trained model generation estimation image 92 and the trained model input estimation image 68 in which the center line 96 based on the backbone and the shoulder line 97 of the subject P are shown are generated, but the present invention is not limited thereto.

For example, the trained model generation estimation image 92 and the trained model input estimation image 68 in which the center line 96 based on the backbone and the shoulder line 97 of the subject P are shown in the optical image 64 may be generated.

Further, in the above-described embodiment, an example is shown in which the X-ray imaging apparatus 100 is used for X-ray imaging of a chest, but the present invention is not limited thereto. For example, the X-ray imaging apparatus 100 may be used for X-ray imaging a site other than a chest.

Further, in the above-described embodiment, an example is shown in which the X-ray imaging apparatus 100 is configured to perform imaging in a posture (standing position) in which the subject P stands, but the present invention is not limited thereto. For example, the X-ray imaging apparatus 100 may be configured to perform imaging in a posture (lying position) with a subject P laid.

Further, in the above-described embodiment, an example is shown in which the optical imaging unit 40 continuously images the subject P at the time of capturing the X-ray image 63, but the present invention is not limited thereto. For example, the optical imaging unit 40 may be configured to image the subject P at a predetermined timing.

[Aspects]

It will be understood by those skilled in the art that the above-described exemplary embodiments are concrete examples of the following aspects.

(Item 1)

An X-ray imaging apparatus comprising:
- an X-ray irradiation unit including an X-ray tube;
- a detector configured to detect X-rays emitted from the X-ray irradiation unit;
- an image generation unit configured to generate an X-ray image based on the X-rays detected by the detector;
- an optical imaging unit configured to capture an optical image in a direction of a subject and the detector from a side of the X-ray irradiation unit;
- a storage unit configured to store a trained model for outputting determination information for an input image based on the optical image including the subject imaged by the optical imaging unit, the determination information determining a state regarding an imaging range of a predetermined site of the subject or a relative position of the predetermined site to the other site of the subject;
- a control unit configured to acquire the determination information, using the trained model; and
- a notification unit configured to perform notification based on the determination information acquired by the control unit.

(Item 2)

The X-ray imaging apparatus as recited in the above-described Item 1,
- wherein the trained model is configured to receive the input image based on the optical image captured by the optical imaging unit from substantially the same direction as an imaging direction of the X-ray image and output the determination information on the subject in the input image, and
- wherein the control unit is configured to acquire the determination information in the input image using the trained model before emitting X-rays to acquire the X-ray image.

(Item 3)

The X-ray imaging apparatus as recited in the above-described Item 1 or 2,
- wherein the control unit is configured to acquire
- determination information for determining a state regarding an imaging range of an apex area of a lung of the subject, the determination information being outputted from the trained model;
- determination information for determining a state regarding a relative position of the apex area of the lung to a clavicle of the subject;
- determination information for determining a state regarding a relative position of a lung field to a scapula of the subject, or
- determination information for determining a state of internal rotation of an arm of the subject serving an index of overlap between the lung field and the scapula of the subject.

(Item 4)

The X-ray imaging apparatus as recited in the above-described Item 3
- wherein the X-ray irradiation unit includes a collimator for defining an X-ray irradiation field and a collimator lamp for making the X-ray irradiation field visible, and
- wherein the control unit is configured to, using the trained model, acquire determination information for determining a state regarding an imaging range of the apex area of the lung as the predetermined site of the subject, the determining information indicating whether the apex area of the lung of the subject is included in an area of the X-ray irradiation area based on irradiation light from the collimator lamp in the input image.

(Item 5)

The X-ray imaging apparatus as recited in the above-described Item 4 wherein the control unit is configured to generate an extraction image in which a contour of the subject and the X-ray irradiation field included in the optical image captured by the optical imaging unit are extracted, input the extraction image that is the input image to the trained model, and acquire the determination information on the subject as an output result.

(Item 6)

The X-ray imaging apparatus as recited in the above-described Item 3, wherein the control unit is configured to, using the trained model, acquire determination information for determining a state regarding the relative position of the apex area of the lung as the predetermined side of the subject to the clavicle as the other site of the subject, the determination information indicating whether the apex area of the lung and the clavicle of the subject overlap with each other in the input image.

(Item 7)

The X-ray imaging apparatus as recited in the above-described Item 6 wherein the control unit is configured to generate an estimation image in which a shoulder line of the subject included in the optical image captured by the optical imaging unit is estimated, input the estimation image to the trained model, the estimation image being the input image, and acquire the determination information of the subject, the determination information being an output result.

(Item 8)

The X-ray imaging apparatus as recited in the above-described Item 3, wherein the control unit is configured to, using the trained mode, acquire state information on the relative position of the lung field as the predetermined site of the subject to a scapula as the other side, the state information indicating whether the lung field and the scapula of the subject overlap with each other in the input image.

(Item 9)

The X-ray imaging apparatus as recited in the above-described Item 8, wherein the control unit is configured to generate an estimation image in which an internal rotation state of an arm of the subject included in the optical image captured by the optical imaging unit is estimated, input the estimation image to the trained model, the estimation image being the input image, and acquire the determination information on the subject, the determination information being an output result.

(Item 10)

The X-ray imaging apparatus as recited in the above-described Item 3, wherein the control unit is configured to acquire, using the trained model, status information on internal rotation of an arm as an index, the status information indicating whether the arm of the subject is rotated toward an inside of the body in the input image.

(Item 11)

The X-ray imaging apparatus as recited in the any one of the above-described Items 1 to 10, wherein the optical imaging unit is mounted on a collimator that defines an X-ray irradiation field included in the X-ray irradiation unit.

(Item 12)

The X-ray imaging apparatus as recited in any one of the above-described Items 1 to 11, wherein the notification unit includes a display unit configured to display information based on the determination information acquired by the control unit.

The invention claimed is:

1. An X-ray imaging apparatus comprising:
   an X-ray irradiation unit including an X-ray tube;
   a detector configured to detect X-rays emitted from the X-ray irradiation unit;
   an image generation unit configured to generate an X-ray image based on the X-rays detected by the detector;
   an optical imaging unit configured to capture an optical image in a direction of a subject and the detector from a side of the X-ray irradiation unit;
   a storage unit configured to store a trained model for outputting determination information for an input image based on the optical image including the subject imaged by the optical imaging unit, the determination information determining a state regarding an imaging range of a predetermined site of the subject or a relative position of the predetermined site to another site of the subject;
   a control unit configured to acquire the determination information, using the trained model; and
   a notification unit configured to perform notification based on the determination information acquired by the control unit,
   wherein the control unit is configured to acquire:
      determination information for determining a state regarding an imaging range of apex area of a lung of the subject, the determination information being outputted from the trained model,
      determination information for determining a state regarding a relative position of the apex area of the lung to a clavicle of the subject,
      determination information for determining a state regarding a relative position of a lung field to a scapula of the subject, or
      determination information for determining a state of internal rotation of an arm of the subject serving an index of overlap between the long field and the scapula of the subject.

2. The X-ray imaging apparatus as recited in claim 1,
   wherein the trained model is configured to receive the input image based on the optical image captured by the optical imaging unit from the same direction as an imaging direction of the X-ray image and output the determination information on the subject in the input image, and
   wherein the control unit is configured to acquire the determination information in the input image using the trained model before emitting X-rays to acquire the X-ray image.

3. The X-ray imaging apparatus as recited in claim 1,
   wherein the X-ray irradiation unit includes a collimator for defining an X-ray irradiation field and a collimator lamp for making the X-ray irradiation field visible, and
   wherein the control unit is configured to, using the trained model, acquire the determination information for determining the state regarding the imaging range of the apex area of the lung as the predetermined site of the subject, the determining information indicating whether the apex area of the lung of the subject is included in an area of the X-ray irradiation field based on irradiation light from the collimator lamp in the input image.

4. The X-ray imaging apparatus as recited in claim 3, wherein the control unit is configured to:
generate an extraction image in which a contour of the subject and the X-ray irradiation field included in the optical image captured by the optical imaging unit are extracted;
input the extraction image that is the input image to the trained model; and
acquire the determination information on the subject as an output result.

5. The X-ray imaging apparatus as recited in claim 1, wherein the control unit is configured to;
using the trained model, acquire determination information for determining a state regarding the relative position of the apex area of the lung as the predetermined site of the subject to the clavicle as the another site of the subject, the determination information indicating whether the apex area of the lung and the clavicle of the subject overlap with each other in the input image.

6. The X-ray imaging apparatus as recited in claim 5, wherein the control unit is configured to:
generate an estimation image in which a shoulder line of the subject included in the optical image captured by the optical imaging unit is estimated;
input the estimation image to the trained model, the estimation image being the input image; and
acquire the determination information of the subject, the determination information being an output result.

7. The X-ray imaging apparatus as recited in claim 1, wherein the control unit is configured to:
using the trained model, acquire state information on the relative position of the lung field as the predetermined site of the subject to a scapula as the another side, the state information indicating whether the lung field and the scapula of the subject overlap with each other in the input image.

8. The X-ray imaging apparatus as recited in claim 7, wherein the control unit is configured to:
generate an estimation image in which an internal rotation state of an arm of the subject included in the optical image captured by the optical imaging unit is estimated;
input the estimation image to the trained model, the estimation image being the input image; and
acquire the determination information on the subject, the determination information being an output result.

9. The X-ray imaging apparatus as recited in claim 1, wherein the control unit is configured to acquire:
using the trained model, status information on internal rotation of an arm as an index, the status information indicating whether the arm of the subject is rotated toward an inside of a body of the subject in the input image.

10. The X-ray imaging apparatus as recited in claim 1, wherein the optical imaging unit is mounted on a collimator that defines an X-ray irradiation field included in the X-ray irradiation unit.

11. The X-ray imaging apparatus as recited in claim 1, wherein the notification unit includes a display unit configured to display information based on the determination information acquired by the control unit.

* * * * *